United States Patent [19]
Eichardt et al.

[11] Patent Number: 5,949,538
[45] Date of Patent: Sep. 7, 1999

[54] LONGITUDINALLY OR TRANSVERSELY HEATED TUBULAR ATOMIZING FURNACE

[75] Inventors: Klaus Eichardt, Jena; Bernd Thiele, Troisdorf, both of Germany

[73] Assignee: SGL Carbon AG, Wiesbaden, Germany

[21] Appl. No.: 09/038,593

[22] Filed: Mar. 11, 1998

Related U.S. Application Data

[63] Continuation of application No. PCT/EP97/03500, Jul. 3, 1997.

[51] Int. Cl.$^6$ .................................................... G01N 21/74
[52] U.S. Cl. ............................................................ 356/312
[58] Field of Search ...................................... 356/312, 244

[56] References Cited

U.S. PATENT DOCUMENTS

| | | | |
|---|---|---|---|
| 4,303,339 | 12/1981 | Gläser et al. | 356/312 |
| 4,826,318 | 5/1989 | Guenther et al. | 356/312 |
| 4,946,278 | 8/1990 | Hütsch et al. | 356/312 |
| 4,961,645 | 10/1990 | Schlemmer et al. | 356/312 |
| 4,968,141 | 11/1990 | Tamm et al. | 356/312 |
| 4,971,438 | 11/1990 | Hütsch et al. | 356/312 |
| 5,083,864 | 1/1992 | Hütsch et al. | 356/312 |
| 5,367,374 | 11/1994 | Eichardt et al. | 356/312 |

FOREIGN PATENT DOCUMENTS

| | | |
|---|---|---|
| 0 321 879 A2 | 6/1989 | European Pat. Off. . |
| 0 408 872 A2 | 1/1991 | European Pat. Off. . |
| 0 442 009 A1 | 8/1991 | European Pat. Off. . |
| 29 24 123 C2 | 12/1980 | Germany . |
| 233 190 | 9/1984 | Germany . |
| 35 45 635 A1 | 6/1987 | Germany . |
| 8 714 670 | 2/1988 | Germany . |
| 37 22 379 A1 | 3/1988 | Germany . |
| 87 14 926 | 3/1988 | Germany . |
| 88 03 144 | 6/1988 | Germany . |
| 38 23 346 A1 | 1/1990 | Germany . |
| 42 43 767 C2 | 6/1994 | Germany . |
| 2 158 265 | 11/1985 | United Kingdom . |

OTHER PUBLICATIONS

"Electrothermal atomization—the way toward absolute methods of atomic absorption analysis" (B.V. L'vov), Spectrochimica Acta, vol. 33 B, pp. 153–193.

"Time–dependent temperature distribution of graphite–tube atomizers" (Falk et al.), Spectrochimica Acta, vol. 40 B, No. 3, 1985, pp. 533–542.

*Primary Examiner*—F. L. Evans
*Attorney, Agent, or Firm*—Herbert L. Lerner; Laurence A. Greenberg

[57] ABSTRACT

A transversely or longitudinally heated atomizing furnace for flameless atomic absorption spectrometry. The atomizing furnace has a tube furnace segment and a specimen support disposed in the tube furnace segment. The specimen support is rigidly fixed in the tube furnace. For that purpose, the specimen support has on its underside a central peg or foot which is fixed in a complementary depression or recess formed centrally in the inner wall of the tube furnace, approximately opposite the sample insertion opening. The specimen support and the tube furnace segment are formed from electrographite. The gas-accessible surfaces of the specimen support and the tube furnace segment are coated with pyrocarbon. The two members are non-detachably connected to each other by means of the pyrocarbon coating. The specimen support extends over as large as possible a portion of the length of the tube furnace. On its upper side, the specimen support is formed with a trough that can receive up to 50 $\mu$l of solution to be analyzed. The solid mass of the specimen support is structurally minimized.

19 Claims, 8 Drawing Sheets

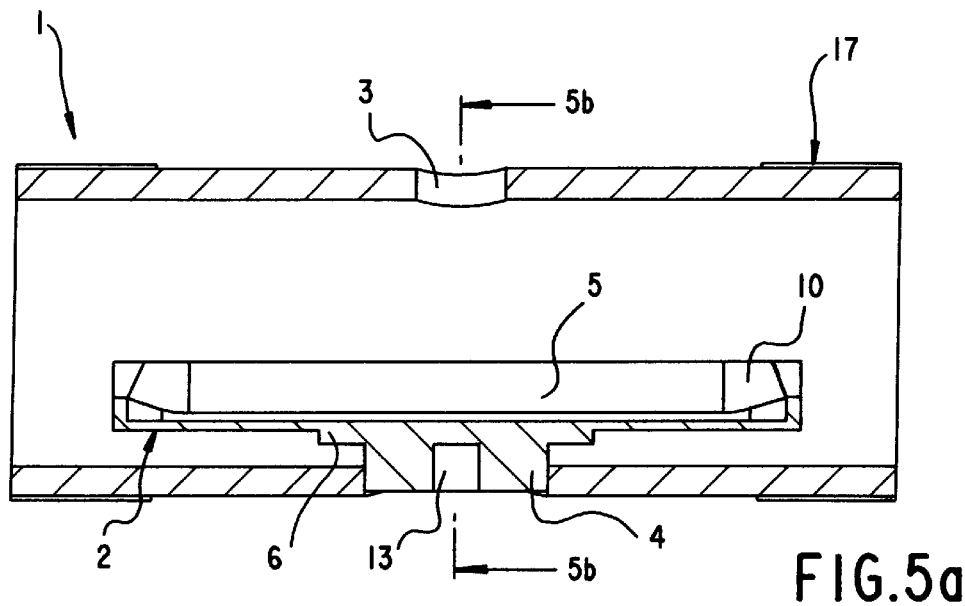
FIG.5a
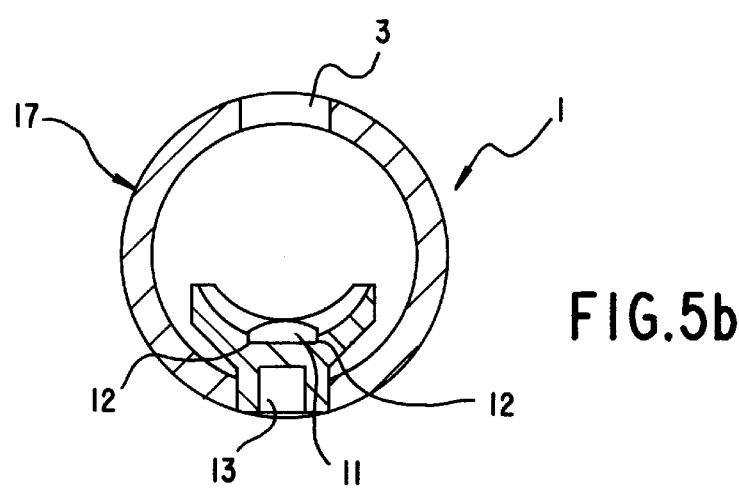
FIG.5b
FIG.5c

LONGITUDINALLY OR TRANSVERSELY HEATED TUBULAR ATOMIZING FURNACE

CROSS-REFERENCE TO RELATED APPLICATION

This is a continuation of copending international application PCT/EP97/03500, filed Jul. 3, 1997, which designated the United States.

BACKGROUND OF THE INVENTION

FIELD OF THE INVENTION

The invention relates to atomizing furnaces for spectroscopy and, more specifically, to such an atomizing furnace formed of carbon material which is electrically transversely or longitudinally heated. The furnace is assembled from a tube furnace segment formed with a sample insertion opening and a separately produced specimen support. The tube furnace segment, in whose interior chamber the atomization takes place and which has on the outside contact elements for connection for electrical heating, is formed with a recess for receiving a peg located on the underside of the specimen support. The recess is formed in the inside wall at the side lying approximately opposite to the sample insertion opening. The specimen support, which serves for the uptake and delayed vaporization of the sample to be analyzed, is disposed and held in the inside wall of the tube furnace essentially outside the path of the working beam. The specimen support is held in the tube furnace segment by a peg that extends from its outside wall downwardly to the wall of the tube furnace segment and the specimen support being held by means of this by insertion in a recess in the wall of the tube furnace segment corresponding to the shape of the peg. Atomizing furnaces of this type are preferably used for flameless atomic absorption spectrometry on the basis of graphite tube technology (GF-AAS) for the vaporization and the atomization of solid and liquid samples.

It is an essential object in GF-AAS to delay the thermal atomization of the sample with respect to the heating of the inner chamber of the atomizing furnace. This ensures that the constituents of the sample vaporize under approximately stabilized temperature conditions and are atomized suddenly and cannot precipitate on comparatively cooler parts of the walls of the inner atomization chamber. This object is satisfied in the prior art disposing a specimen support in the inner furnace chamber. In the ideal case, the specimen support should for this purpose be constructed and fixed in the furnace in such a way that it is heated neither by heat conduction nor by Joulean heat, but instead exclusively by radiant heat from the inside wall of the furnace. An configuration with a longitudinally heated atomizing furnace with a specimen support—which configuration, however, fulfilled the above-mentioned requirements to only a certain extent—was first suggested by L'vov, 33B Spectrochimica Acta, pp 153–93; Pergamon Press, U.K. 1978.

Further developments of specimen supports for longitudinally heated atomizing furnaces appeared in various patent publications, including German patent DE 29 24 123, German utility models GM 87 14 926.5, GM 88 03 144.6, German published, non-prosecuted applications 37 22 379 and 38 23 346.0, and in European published application EP 0 442 009. All of those teachings, however, are still subject to the essential disadvantages with regard to the above-mentioned requirements.

A further, improved specimen support for a longitudinally heated atomizing furnace is described in the East German publication DD 233 190 A (West German publication number 35 45 635). The support is point-fixed by way of a pin-like support disposed asymmetrically with respect to the tube furnace center and is inserted into an indentation formed in the inside wall of the tube furnace. The specimen support can, however, be removed from the tube furnace at any time. One of the express objects of this disclosure was that atomizing furnace and specimen support do not form a non detachable unit in the operative final state of production, because the specimen support itself can be inserted and removed by a manipulator. The result is that the position of the specimen support in the atomizing furnace is not positively fixed particularly in the case of shaking or in the presence of strong magnetic fields. Tests by the applicant resulted in uncontrolled wall contacts of the specimen support and thus current conduction and heat conduction between the outside edges of the specimen support and the inside wall of the furnace. This consequently led to irreproducible relationships from measurement to measurement. The specimen support is designed to receive only small volumes of substance to be analyzed (<10 $\mu$l) and is to be produced only from vitreous carbon or pyrocarbon. Vitreous carbon and solid pyrolytic carbon can be used as materials for specimen supports to only a limited degree, because the analytical determination of refractory-carbide-forming GF-AAS substances for analysis from surfaces of this type is not possible, the required material purities can be realized only with difficulty, and the cost-performance ratio is unfavorable for the user.

Transversely heated atomizing furnaces were first introduced in 1987 (cf. German utility model GM 87 14 670). European patent publication EP 0 321 879 A2 (corresponding to U.S. Pat. Nos. 4,968,141 and 4,961,645) describes an atomizing furnace with a specimen support in a longitudinally heated embodiment and in a transversely heated embodiment, which specimen support is connected to the inside wall of the furnace in a non detachable manner by way of a web which lies symmetrically with respect to the center of the furnace.

Specimen support and furnace form a material structural unit, which is produced from one crude body.

The specimen-holder portion extends only over a central region of the furnace portion. Consequently, there is only a small receiving volume for the substance to be analyzed. The connecting web itself has a plurality of transverse bores as a material-reducing measure. An atomizing furnace of this type, consisting of a solid graphite blank can be produced only at great technical expenditure. This obviously has a negative effect on the price to the user for this wear part.

Specimen supports with supporting rings for transversely heated atomizing furnaces in accordance with German Patent 42 43 767 C2 can likewise be produced only at high cost and with great technical expense, although both the specimen support and the furnace can each be produced as a component part.

SUMMARY OF THE INVENTION

It is accordingly an object of the invention to provide a longitudinally or transversely heated tubular atomizing furnace, which overcomes the above-mentioned disadvantages of the prior art devices and methods of this general type and which is to so construct specimen supports and adapt them to the conditions in the atomizing furnaces surrounding them that the above-mentioned technical and analysis deficiencies attendant to the prior art systems no longer occur in practice. In particular, the specimen support is to be constructed and accommodated in the tube furnace in such a way that during the analysis, there are obtained with this novel configuration measurement signals which are formed more sharply in comparison with the prior art, and a fast decay of these signals to the noise level of the measurement configuration takes place, i.e. so that more precise analysis results are achieved than hitherto and a plurality of such precise analyzing processes can be carried out one after the other.

It is a further object of the invention to provide a combination of tube furnace-specimen support made of a material which permits proper detection for all elements which can typically be analyzed by GF-AAS, namely 59 elements.

With the foregoing and other objects in view there is provided, in accordance with the invention, an atomizing furnace, comprising:

- a tube furnace segment defining a furnace chamber and having a sample insertion opening formed therein, the tube furnace segment having contact elements on an outside thereof for electrically heating the furnace chamber;
- a specimen support produced separately from the tube furnace segment, the specimen support being formed with a trough for receiving specimen sample, and including a peg disposed at an underside thereof substantially centrally below the trough;
- the tube furnace segment being formed with a recess for receiving the peg of the specimen support, the recess being formed in the chamber substantially centrally along a length of the furnace chamber; and
- the peg of the specimen support being non-releasably secured in the recess.

In accordance with an added feature of the invention, the tube furnace segment and the separately produced specimen support are commonly coated with a layer of pyrocarbon deposited thereon after the specimen support and the tube furnace segment were joined together.

In accordance with an additional feature of the invention, the specimen support and the tube furnace segment consist of mutually similar or identical materials having substantially similar or identical mechanical, physical, and chemical properties.

In accordance with another feature of the invention, the specimen support and the tube furnace segment have substantially similar coefficient of thermal expansion, and substantially similar material characteristic values for porosity and a performance on being coated with pyrocarbon.

In accordance with a further feature of the invention, the specimen support and the tube furnace segment are formed of electrographite, and the specimen support and the tube furnace segment have gas-accessible surfaces defined thereon which are coated with pyrocarbon.

In accordance with again an added feature of the invention, the recess for receiving the peg is formed in the tube furnace segment substantially opposite from the sample insertion opening.

In accordance with again an additional feature of the invention, the peg has a cross-section which deviates from circular, and the recess in the tube furnace segment has a complementary shape.

In accordance with again another feature of the invention, the peg has a cross-section discretely decreasing in steps towards the inner wall surface of the tube furnace segment, with at least one of the steps having a larger cross-section than the recess for receiving the peg, for defining a distance between the trough of the specimen support and the inner wall surface of the tube furnace segment.

In accordance with again an additional feature of the invention, the specimen support, except for the trough for receiving the specimen samples, is formed with substantially flat faces and substantially straight edges.

With the above and other objects in view there is further provided, in accordance with the invention, a method of producing an atomizing furnace for use in spectroscopy, the method which comprises:

- producing a tube furnace segment with a furnace chamber having an inner wall surface, with a sample insertion opening, with contact elements on an outside thereof for electrically heating the furnace chamber, and with a recess substantially centrally along a length of the furnace chamber;
- producing a specimen support separately from the tube furnace segment, the specimen support having a trough for receiving specimen sample, and a peg disposed at an underside thereof substantially centrally below the trough;
- inserting the peg of the specimen support into the recess formed in the furnace chamber of the tube furnace segment; and
- non-releasably securing the peg in the recess and rigidly attaching the specimen support to the tube furnace segment by coating with pyrocarbon all gas-accessible surfaces of the specimen support and the tube furnace segment.

In accordance with a concomitant feature of the invention, the tube furnace segment and the specimen support are produced from the same electrographite material.

In other words, the furnace body and the specimen support consist of electrographite with the same or similar physical and chemical properties. They are each produced separately and only then joined together. After they are joined to one another, the gas-accessible surfaces of the combination specimen support/furnace body are coated with a pyrocarbon layer. As a result, the porous surfaces of the electro-graphite are sealed fluid-tight. Thereafter, the combination is ready for use. The specimen support is constructed as a shell and has on its underside a peg, which is arranged centrally with regard to the longitudinal extent and the transverse extent of said specimen support and faces the lower portion of the inside wall of the furnace. The peg is inserted into the depression—here generically referred to as a recess—which complements the shape of the peg and is located longitudinally centered on the inside of the furnace portion, in the furnace wall approximately opposite the sample insertion opening. As a result of the shape of the peg, which is preferably non-circular, and the depression in the inner wall of the furnace that is complementary thereto, the specimen support is fixed in the furnace in a form-locking manner. The pyrocarbon coating additionally fixes the two structural components together in an integral, material-locking, well-defined and reproducible fashion. The specimen support is of minimal mass and its trough-like or shell-like portion preferably extends over as great a portion of the inner furnace chamber available to it as possible.

In accordance with again a further feature of the invention, the atomizing furnace is transversely heated and the tube furnace segment has a given length, and the specimen support extends over at least 75% (preferably more than 80%) of the given length of the tube furnace segment. Where the atomizing furnace is longitudinally heated, the specimen support extends over 50% to 85% of the given length of the tube furnace segment. In other words, where it is considered sufficient for achieving the operational requirements of the assembly, the specimen support may even have less than the full length of the chamber.

In accordance with yet an added feature of the invention, the specimen support is formed with walls having thicknesses of 0.5 mm or less.

In accordance with yet an additional feature of the invention, the trough is formed in a shell-like portion of the specimen support, the shell-like portion having walls with thicknesses of less than 0.3 mm.

The trough or shell-like portion of the specimen support is able to receive up to 50 μl of solution to be analyzed in the case of transversely heated furnaces, and up to 40 μl of solution to be analyzed in the case of longitudinally heated furnaces. All parts are constructed in such a way that their production requires as little expenditure as possible.

In accordance with yet another feature of the invention, the peg of the specimen support has a downwardly open and axially extending hollow space formed therein.

In accordance with yet a further feature of the invention, the trough has a depression formed therein along a deepest zone of the trough. In a specific embodiment, the depression is a longitudinal groove extending over the entire length of the trough of the specimen support.

The body of the specimen support is essentially constructed from the two function-determining portions peg and sample shell and has a minimum mass, typically, and unlike known solutions, less than 100 mg. The special connection of the specimen support to the tube furnace by way of a centrally arranged peg, the mass of which has been minimized, in combination with the small mass of the sample shell, means a considerable reduction in heat conduction. Electrical heating by Joulean heat is essentially prevented in this configuration. As a result of this, after the desired time-delayed heating of the inside wall of the furnace, a sample to be analyzed that is located in the sample trough is heated to atomization temperature extremely quickly by radiant heat alone. As the absence of memory effects working with the arrangement in accordance with the invention shows (see in this respect FIG. 9), the substance to be analyzed that is placed into the through is completely vaporized, and after the measurement process is also removed completely from the atomization zone of the tube furnace.

The shell-like portion of the specimen support, which is preferably designed to receive volumes of substance to be analyzed of up to 50 μl, preferably has along its shell base an additional groove having preferably perpendicular walls. This groove serves as an additional obstacle to prevent solutions to be analyzed from running off.

As noted, the above-described configuration according to the invention can be used both for transversely heated and for longitudinally heated atomizing furnaces, and for working with both liquid and solid substances to be analyzed without structural alterations to the specimen support.

As a result of the unalterable fixing of the specimen support in the tube furnace, which is effected by the manufacturer, there are considerable advantages during handling and during working with the analytic system in accordance with the invention, because, for example, damage to or incorrect alignments of the sensitive specimen support are ruled out. When working analytically with the arrangement in accordance with the invention, practically no more memory effects are established. It is consequently possible to carry out a large number of analysis procedures one after the other. This results in cost advantages for the user.

By reducing the contact surfaces between the furnace and the specimen support to a technically feasible minimum, a considerable improvement in comparison with the prior art systems (DE-PS 29 24 123; DE-GM 87 14 926.5; DE-OS 37 22 379; DE-GM 88 03 144.6; DE-OS 38 23 346.0; EP 0 442 009 A1) with their comparatively large contact surfaces has been achieved.

The novel fastening of the specimen support in the tube furnace additionally ensures a maximum time delay in heating the specimen support in direct comparison to the heating of the inside wall of the atomizing furnace.

The novel combination permits charging and atomizing a very large amount of substance of up to 50 μl, in connection with a maximum heating rate of equal to or greater than 2000 K/s. In this connection, the heating occurs after a desired delay with respect to the heating of the inside wall of the furnace.

By using polycrystalline electrographite of uniform technical quality in order to form the furnace and specimen support, and as a result of the uniform pyrolytic coating which takes place after mechanical assembly, it is possible to analyze all 59 of the elements of the periodic system that can be analyzed with GF-AAS. Only with the analysis of refractory elements such as V, Ti, Si, for example, do small memory effects occur, which can be controlled by known measures.

The analytic system in accordance with the invention exhibits good long-term stability of sensitivity and reproducibility (relative standard deviation (RSD) less than 2% for diluted acidic standard solutions) and an extended linear concentration operating range with regard to the time-integrated extinction (surface integral of the signal variation) necessitated by the method.

By using electrographite as basic material for the production of specimen support and tube furnace and the construction of the portions in a manner suited to rational production, expenditure on production that is lower than that of the prior art is achieved. From this results a further cost advantage for the user.

The combination of tube furnace segment and specimen support is constructed in such a way that the specimen support is arranged inside the tubular portion so as to lie substantially outside the optical beam path and have only one place of attachment, which is located on the common central axis of the two portions.

In this way, geometrical symmetry of the two components with respect to each other is maximized for transversely heated and for longitudinally heated tube furnaces and current conduction through the specimen support is completely avoided. By means of the hollow-shell trough construction of the specimen support over the greater part of the whole length of the tube furnace, the introduction and reliable protection of a maximum volume of substance to be analyzed is rendered possible.

The peg serving to fix the specimen support in the tube furnace segment advantageously has a non circular cross section in order to position the specimen support in a complementary depression in the tube furnace in a manner such that it is protected against torsion. Apart from this, the peg is constructed so as to have at least two steps and only the portion thereof that faces the inside wall of the furnace is located in the depression in the inside wall of the furnace. The broader portion of the peg rests on the inside wall of the furnace and holds the shell-like portion of the specimen support at a distance from the inside wall of the furnace. The inside of the peg can have, starting from its lower face, a hollow space, preferably in the form of a circular or oval countersinking. The size of the hollow space and consequently the effectively active cross-sectional area of the peg permit an adjustment of the heat conduction with regard to an optimal delay with respect to time and a minimization of the total mass of the specimen support. The place of attachment for this connecting web in the case of longitudinally and transversely heated furnaces is also at the same time in what is relatively speaking the coldest region of the inside wall of the atomizing furnace during the heating process. See the tests published by Falk et al., 40B Spectro-chimica Acta No. 3, pp. 533–42, Pergamon Press, U.K., 1985, for longitudinally heated furnaces, and applicants' measurements for transversely heated furnaces (FIG. 4).

The configuration of the invention ensures as well that the desired time-delayed heating of the sample takes place virtually exclusively by radiant energy, which is radiated only from the inside wall of the respective tubular atomizing furnace portion.

Other features which are considered as characteristic for the invention are set forth in the appended claims.

Although the invention is illustrated and described herein as embodied in longitudinally or transversely heated tubular atomizing furnace, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

BRIEF DESCRIPTION OF THE DRAWINGS

FIG. 1b is a cross sectional view through the atomizing furnace taken along the sectional plane A—A of FIG. 1a;

FIG. 5a is a longitudinal sectional view taken through an atomizing furnace for longitudinal heating or for transverse heating, with an additional longitudinal groove on the base of the specimen support;

FIG. 5b is a cross sectional view through the atomizing furnace of FIG. 5a for the longitudinally heated embodiment;

FIG. 5c is a similar view relating to a transversely heated embodiment;

FIG. 6a is a top perspective view of the specimen support of a configuration according to FIG. 5a;

DESCRIPTION OF THE PREFERRED EMBODIMENTS

Figure 1A:
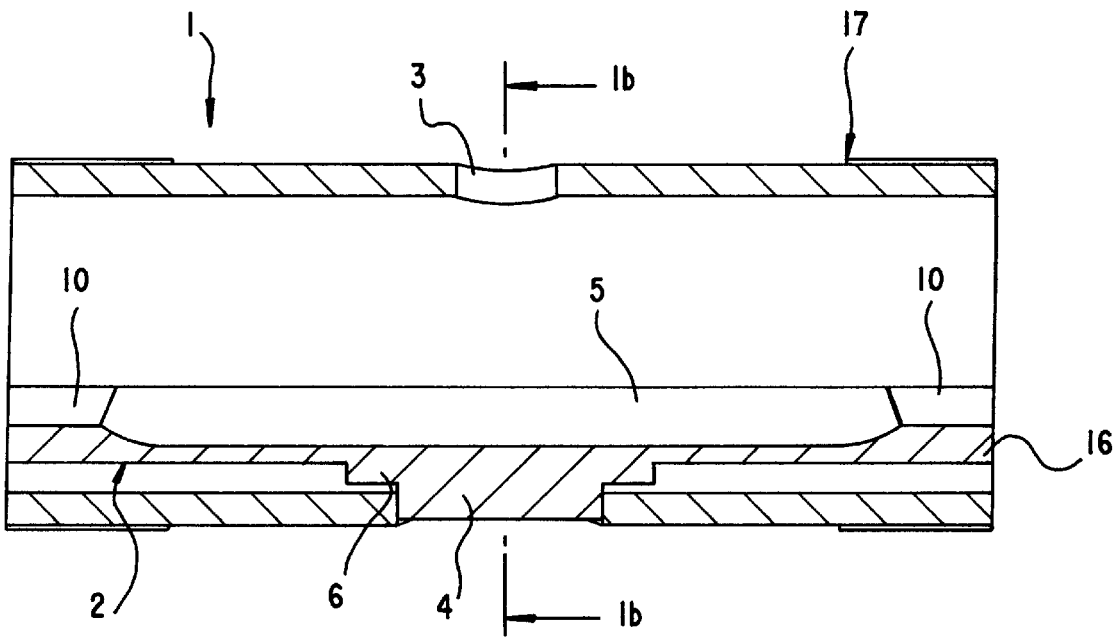
FIG. 1a is a longitudinal sectional view taken through an atomizing furnace in accordance with the invention.

Referring now to the figures of the drawing in detail and first, particularly, to FIG. 1a thereof, there is seen a tubular atomizing furnace 1 consisting of electrographite coated with pyrocarbon. A specimen support 2 is located in the tube furnace segment 17. The support 2 is mounted in a recess in the tube furnace segment 17, opposite a sample insertion opening 3 in the tube furnace segment 17, by means of a supporting foot or peg 4. Similar to the tube furnace segment 17, the specimen support 2 consists of electro-graphite. After it was placed in the tube furnace segment 17, the specimen support 2 was coated, together with the tube furnace segment, with pyrocarbon. The pyrocarbon coating is not illustrated as a separate layer. Instead, the outer wall indicated by the single boundary lines of the respective components are intended to illustrate both the structural boundary and the pyrocarbon coating.

The specimen support 2 has, in its platform 16, a shell-type recess 5, i.e. a trough 5 for receiving a specimen sample. The ends 10 of the trough 5 are not so deeply worked, so that edges result which form run-off obstacles for sample liquid. The peg 4 has a stepped structure so that an intermediate stage 6 ensures that the required constant distance from the inside wall of the tube furnace segment 17 is guaranteed.

Figure 1B:
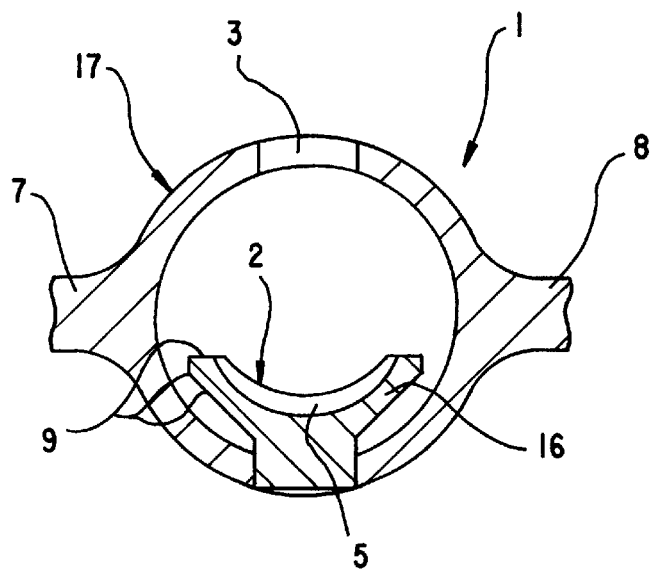

FIG. 1b shows a cross-section through the atomizing furnace 1 shown in FIG. 1a, along the line A—A. Contact pieces 7 and 8 for transverse heating are partly shown. It can be seen here that, with the exception of the trough 5, the specimen support 2 has straight side faces 9, which are technically easy to produce.

Figure 2:
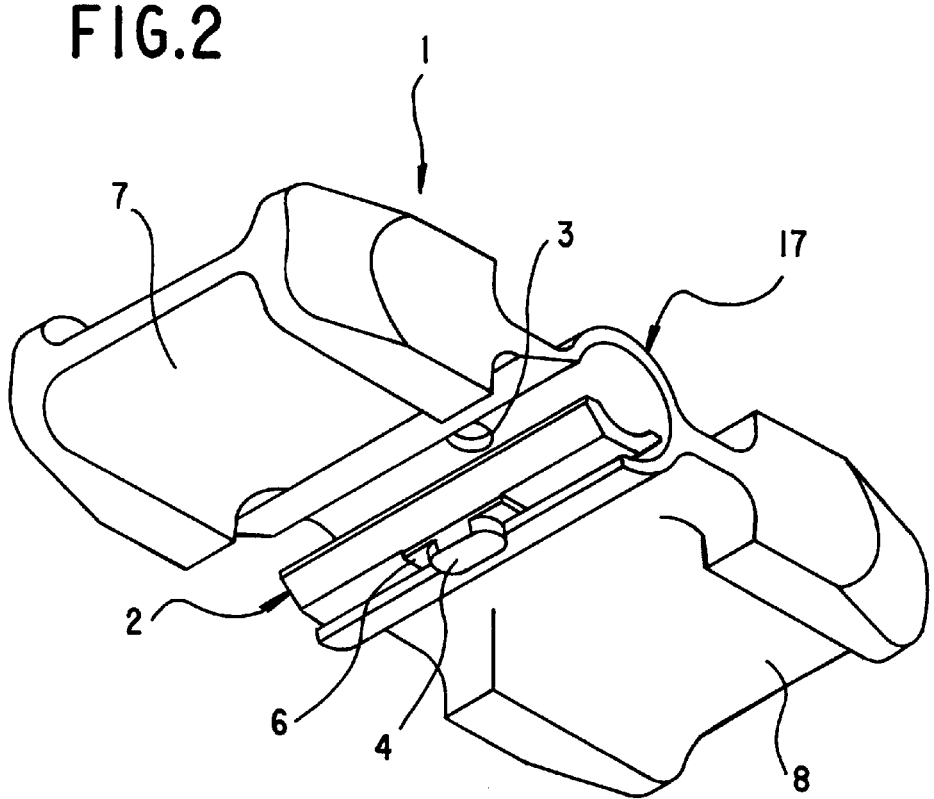
FIG. 2 is a bottom perspective, opened-up view of a transversely heated atomizing furnace in accordance with the invention.
Figure 3:
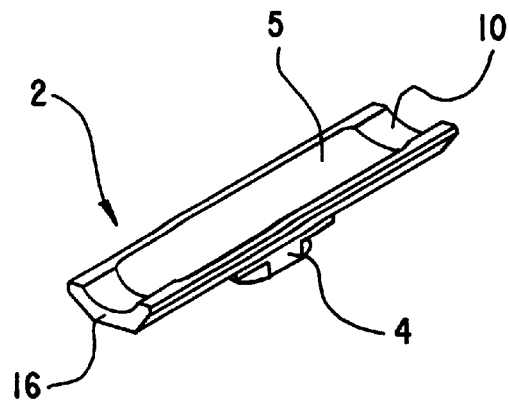
FIG. 3 is a top perspective view of a specimen support in accordance with the invention.

FIG. 2 shows a substantially complete transversely heated furnace 1. The furnace segment 17 is partly broken-away, so as to allow a bottom perspective view onto the specimen support 2. The latter is shown in top perspective in FIG. 3.

The peg or supporting foot 4 has a cross-section which deviates from the circular, in order to avoid mutual rotation when the specimen support 2 is mounted in the tube furnace segment 17.

Figure 4:
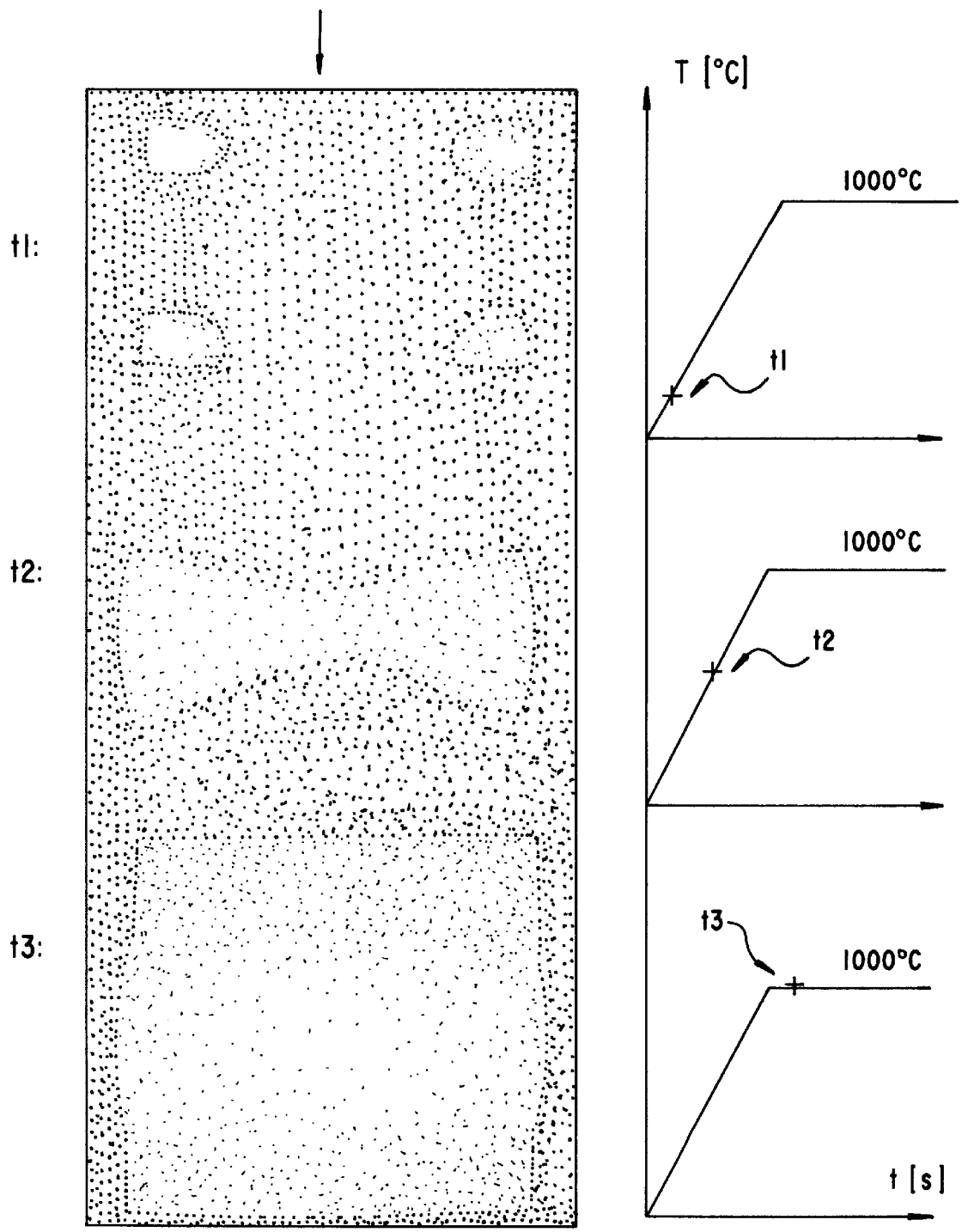
FIG. 4 are three photographs and corresponding temperature over time graphs with reference to heating a transversely heated atomizing furnace in accordance with the invention.

FIG. 4 shows the temperature distribution T(t) of a transversely heated atomizing furnace as a function of the time t during a fast heating process to a predetermined atomization temperature. The distribution is shown at the three stages t1, t2, and t3. It can be seen that the central zone of the tube furnace is advantageously last to be heated to the desired final temperature.

Reference is now had to FIG. 5a, which shows a longitudinal section through a combination tube furnace segment 17 and specimen support 2, for longitudinally and transversely heated furnaces, with a further embodiment of the novel specimen support 2. In order that the sample to be analyzed is received in a secure manner, there is located in the base of the troughed specimen support 2 an additional groove 11. The groove 11 extends across most of the length of the specimen support 2, it is preferably sunk in, and it has substantially perpendicular side walls 12. The base of the groove 11 is preferably formed so as to be level for reasons of ease of production. The peg 4 of the specimen support 2 has a recess 13, which is advantageously bored or sunk in and preferably extends in the axial direction 18, in order to reduce its thermal conduction further and to minimize the mass of the specimen support 2. It is particularly advantageous that all of the wall thicknesses 14 do not exceed a dimension of 0.5 mm, as a result of which the total mass of the specimen support 2 is kept very small.

FIG. 5b reproduces a cross-section through the center of the furnace assembly according to FIG. 5a for a longitudinally heated furnace. FIG. 5c, in contrast, is a corresponding cross-sectional representation for a transversely heated atomizing furnace.

Figure 6A:
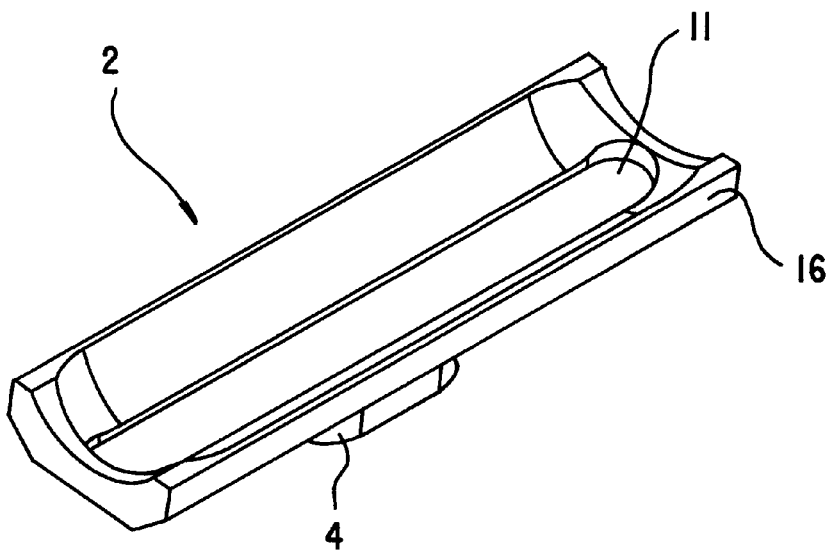
Figure 6B:
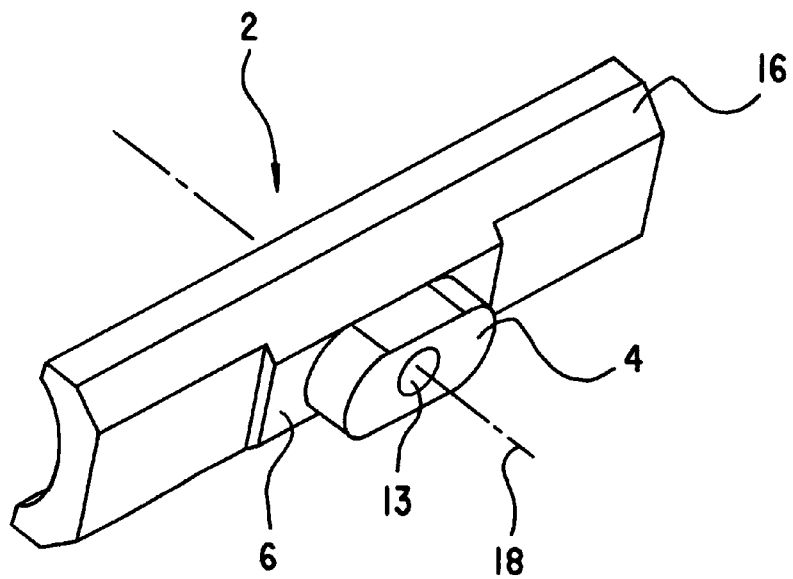
FIG. 6b is a bottom perspective view thereof.

FIGS. 6a and 6b each show a three-dimensional representation of the specimen support 2 of FIGS. 5a to 5c in a top perspective view and a bottom perspective view.

Figure 7A:
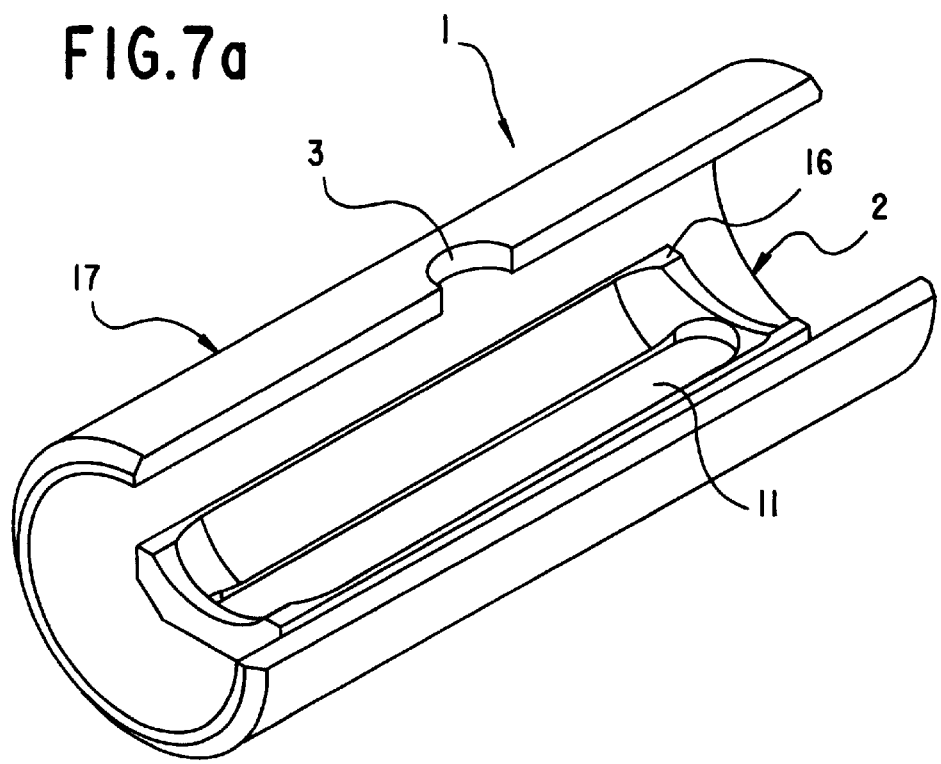
FIG. 7a is a partly broken away, top perspective view of the atomizing furnace of FIG. 5b, viewing the shell-like platform of the specimen support obliquely from above.
Figure 7B:
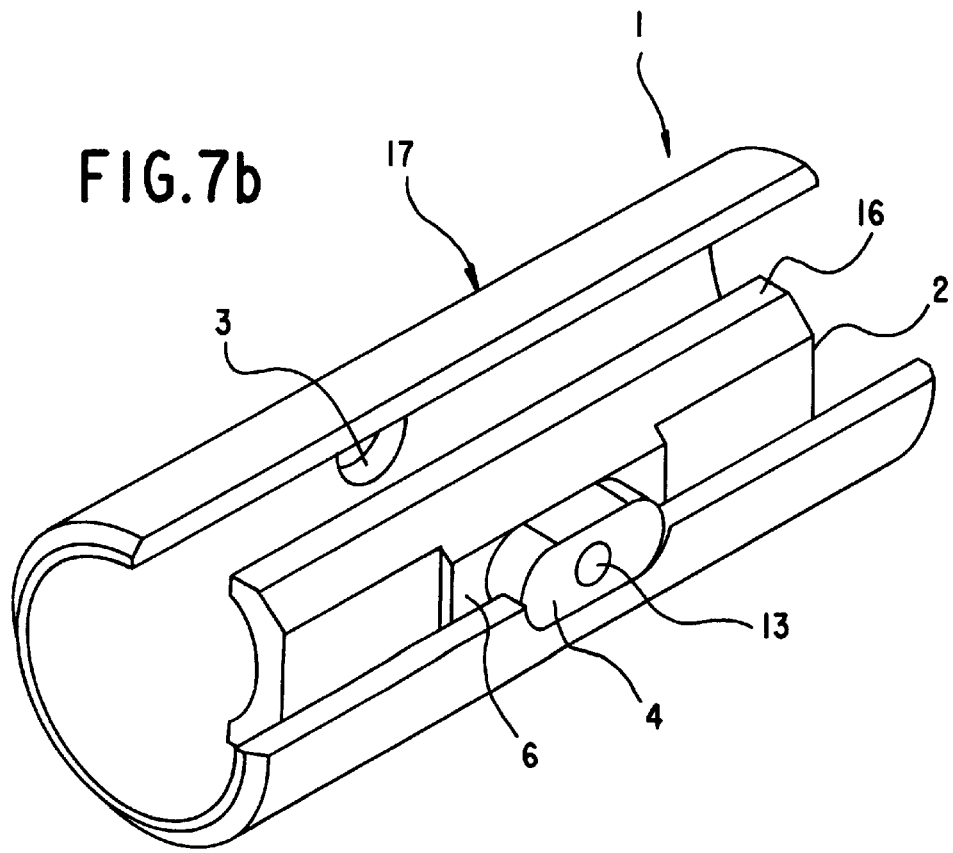
FIG. 7b is a partly broken away, bottom perspective view thereof, showing the peg and the base of the specimen support.

FIGS. 7a and 7b show the specimen supports 2 of FIGS. 5a and 5b as well as FIGS. 6a, 6b, in a longitudinally heated tube furnace segment 17. The furnace segment 17 is partly broken away for open viewing of the support 2.

Figure 8A:
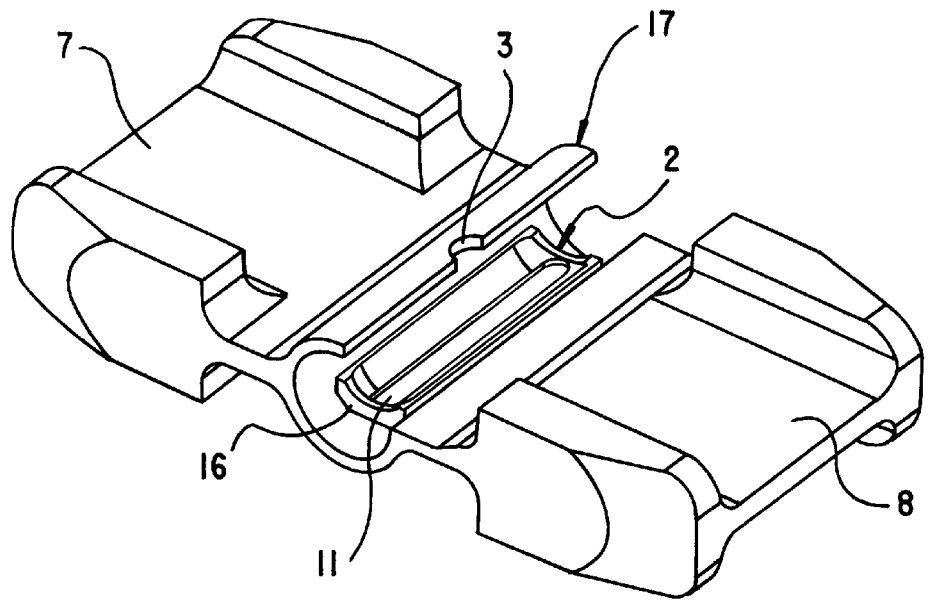
FIGS. 8a and 8b are views similar to those of FIGS. 7a and 7b, respectively, and relating to transversely heated atomizing furnaces.
Figure 8B:
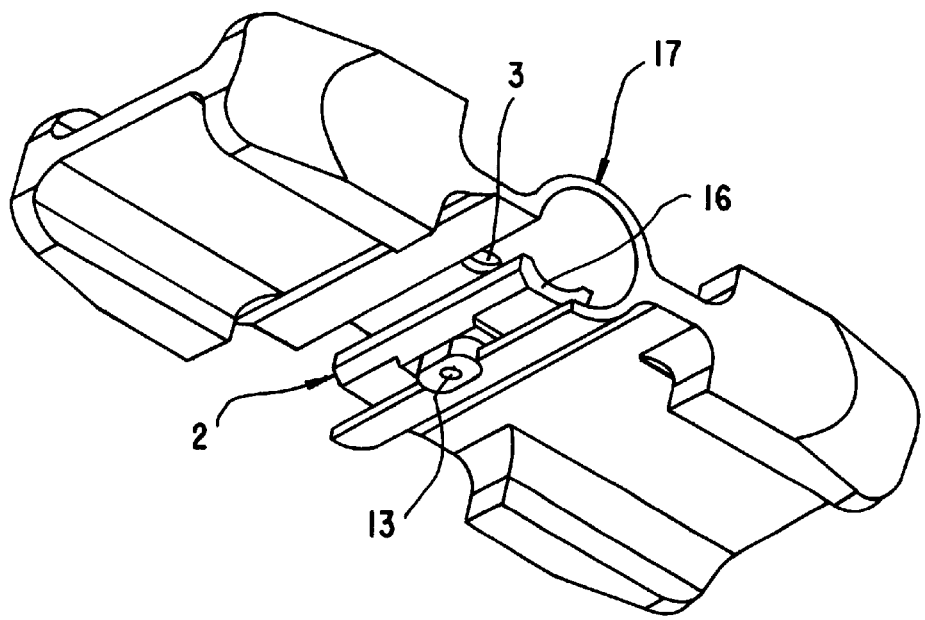

FIGS. 8a and 8b show partly broken-away, perspective representations of a transversely heated atomizing furnace 1. Here, the specimen supports 2 of FIGS. 5a, 5c, 6a and 6b are implemented in the transversely heated furnace 1.

Figure 9:
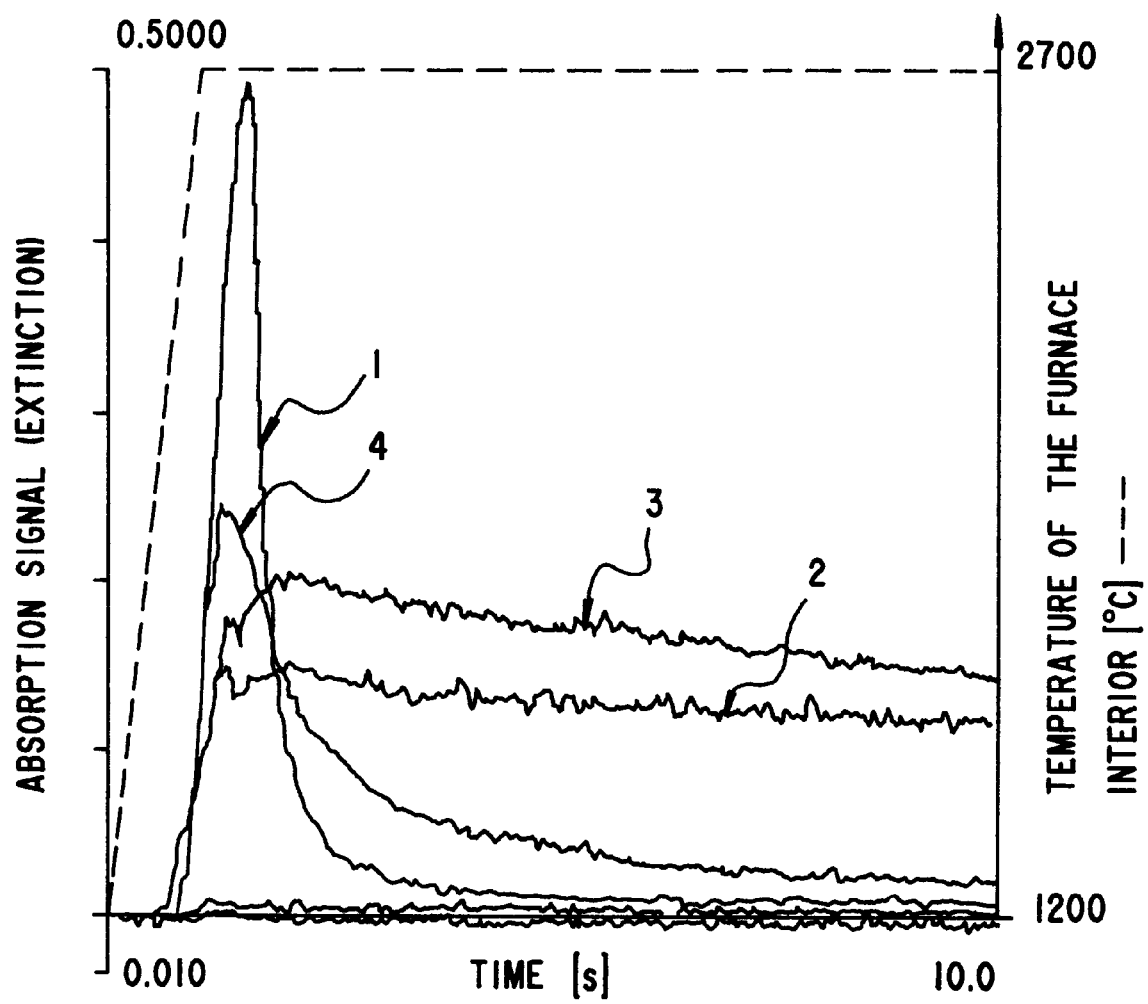
FIG. 9 is a graph showing measurement graphs of various test analyses obtained with different types of specimen supports in atomizing furnaces.

Reference is now had to FIG. 9, which shows absorption signals obtained by means of a furnace configuration according to the invention in comparison with absorption signals obtained with furnace configurations provided with prior art specimen supports. The measurements were carried out with a test solution containing 0.1 $\mu$l/ml vanadium in 0.5% HNO. Different absorption signals or absorption curves, and the temperature progress in the furnace chamber interior, are shown over the time axis for specimen supports of various embodiments in longitudinally heated atomizing furnaces.

Curve 1 resulted from the use of an atomizing furnace in accordance with the invention.

Curve 2 was obtained by measuring with a specimen support of the "fork platform" type made of solid pyrographite material, in accordance with the European publication EP 0 442 009 A.

Curve 3 resulted from the use of a specimen support in accordance with the above-noted East German publication DD 233 190 A (DE-OS 35 45 635). The specimen support is made of glassy carbon, which is detachably held in a bore in the wall of the tube furnace by means of a peg located on its underside.

Curve 4 resulted from the use of a specimen support of the "fork platform" type, which was coated with pyrocarbon.

All curves admittedly have the desired temperature delay with respect to time, often referred to as the "platform effect", relative to the heating of the inside wall of the furnace. In other words, the atomization signals ("peaks") do not result until after the final temperature level has been reached, but they differ clearly in the form and the decay behavior of their signals.

Curve 1 has clearly visible the most sensitive signal and decays as desired to the zero line within the measuring period of 10 seconds. There are therefore no residues remaining in the furnace. The ratio of signal level to noise level is very high and consequently extraordinarily favorable. As a logical result, a high degree of reproducibility of the measurements is ensured.

Curves 2 and 3 show that the atomization signal does not decay in practice. Large amounts of the substance to be analyzed remain in the analysis reactor formed by the specimen support and the tube furnace. Those substantial residual amounts are gradually vaporized and atomized only after the time available for the analysis. Both the structural form of the specimen support and also the material from which the analysis reactor is made are responsible for such a performance. Measurement results of this type cannot be evaluated for analysis purposes, because the analyzing process lasts for too long and the result of the subsequent measurement cycle is falsified by residues of substance to be analyzed that have not been completely vaporized ("memory effect").

Curve 4 was obtained with a configuration in which both the specimen support and the atomizing furnace were coated with pyrocarbon. Nevertheless, the atomization signal which is obtained is much smaller than in FIG. 1 and does not decay completely. The reason for this is that the specimen support is mounted at several points in the furnace and consequently experiences heating which does not come only from the radiation of the inside wall of the furnace. It is namely also heated by undesired electrical transverse heating and increased heat conduction from the inside wall of the furnace. This equally has a damping effect both on signal level and signal area. The signal does not decay completely. Here, as in the case of curves 2 and 3, it will be appreciated that not all of the atoms of the substance to be analyzed that were inserted into the furnace are completely released in an atomization cycle and deliver a signal contribution. Therefore, in this case as well, quantitative determinations of elements forming residues, particularly of refractory elements, are not possible with sufficient accuracy.

The measurement graphs of the curves 1–4 in FIG. 9, therefore, quite impressively underscore the technical progress achieved by the invention. In particular, in operation the atomizing furnace displays good long-term stability in terms of its sensitivity and reproducibility and an extended linear concentration operating period with regard to the time-integrated extinction.

We claim:

1. An atomizing furnace, comprising:
    a tube furnace segment defining a furnace chamber and having a sample insertion opening formed therein, said tube furnace segment having contact elements on an outside thereof for electrically heating said furnace chamber;
    a specimen support produced separately from said tube furnace segment, said specimen support being formed with a trough for receiving specimen sample, and including a peg disposed at an underside thereof substantially centrally below said trough;
    said tube furnace segment being formed with a recess for receiving said peg of said specimen support, said recess being formed in said chamber substantially centrally along a length of said furnace chamber; and
    said peg of said specimen support being non-releasably secured in said recess.

2. The atomizing furnace according to claim 1, wherein said tube furnace segment and said separately produced specimen support are commonly coated with a layer of pyrocarbon deposited thereon after said specimen support and said tube furnace segment were joined together.

3. The atomizing furnace according to claim 1, wherein said specimen support and said tube furnace segment consist of mutually similar material having substantially similar mechanical, physical, and chemical properties.

4. The atomizing furnace according to claim 1, wherein said specimen support and said tube furnace segment consist of identical material having identical mechanical, physical, and chemical properties.

5. The atomizing furnace according to claim 1, wherein said specimen support and said tube furnace segment have substantially similar coefficient of thermal expansion, and substantially similar material characteristic values for porosity and a performance on being coated with pyrocarbon.

6. The atomizing furnace according to claim 1, wherein said specimen support and said tube furnace segment are formed of electrographite, and said specimen support and said tube furnace segment have gas-accessible surfaces defined thereon which are coated with pyrocarbon.

7. The atomizing furnace according to claim 1, wherein said recess for receiving said peg is formed in said tube furnace segment substantially opposite from said sample insertion opening.

8. The atomizing furnace according to claim 1, wherein said peg has a cross-section which deviates from circular, and said recess in said tube furnace segment having a complementary shape.

9. The atomizing furnace according to claim 1, wherein said peg has a cross-section discretely decreasing in steps towards the inner wall surface of the tube furnace segment, with at least one of the steps having a larger cross-section than said recess for receiving said peg, for defining a distance between the trough of said specimen support and the inner wall surface of said tube furnace segment.

10. The atomizing furnace according to claim 1, wherein said specimen support, except for said trough for receiving the specimen samples, is formed with substantially flat faces and substantially straight edges.

11. The atomizing furnace according to claim 1, wherein said tube furnace segment is transversely heated and has a given length, and said specimen support extends over at least 75% of the given length of said tube furnace segment.

12. The atomizing furnace according to claim 1, wherein said tube furnace segment is longitudinally heated and has a given length, and said specimen support extends over 50% to 85% of the given length of said tube furnace segment.

13. The atomizing furnace according to claim 1, wherein said specimen support is formed with walls having thicknesses of ≦0.5 mm.

14. The atomizing furnace according to claim 13, wherein said trough is formed in a shell-like portion of said specimen support, said shell-like portion having walls with thicknesses of less than 0.3 mm.

15. The atomizing furnace according to claim 1, wherein said peg of said specimen support has a downwardly open and axially extending hollow space formed therein.

16. The atomizing furnace according to claim 1, wherein said trough has a depression formed therein along a deepest zone thereof.

17. The atomizing furnace according to claim 16, wherein said depression is a longitudinal groove extending over an entire length of said trough of said specimen support.

18. A method of producing an atomizing furnace for use in spectroscopy, the method which comprises:

producing a tube furnace segment with a furnace chamber having an inner wall surface, with a sample insertion opening, with contact elements on an outside thereof for electrically heating the furnace chamber, and with a recess substantially centrally along a length of the furnace chamber;

producing a specimen support separately from the tube furnace segment, the specimen support having a trough for receiving specimen sample, and a peg disposed at an underside thereof substantially centrally below the trough;

inserting the peg of the specimen support into the recess formed in the furnace chamber of the tube furnace segment; and non-releasably securing the peg in the recess and rigidly attaching said specimen support to said tube furnace segment by coating with pyrocarbon all gas-accessible surfaces of the specimen support and the tube furnace segment.

19. The method according to claim 18, which comprises forming the tube furnace segment and the specimen support from the same electrographite material in the producing steps.

* * * * *

UNITED STATES PATENT AND TRADEMARK OFFICE
CERTIFICATE OF CORRECTION

PATENT NO : 5,949,538
DATED : September 7, 1999
INVENTOR(S) : Klaus Eichardt et al.

It is certified that error appears in the above-identified patent and that said Letters Patent is hereby corrected as shown below:

item [30] should read as follows:

| July 11, 1996 | [DE] | Germany .......... 296 12 065.0 |
| Apr. 19, 1997 | [DE] | Germany .......... 197 16 492.7 |

Signed and Sealed this

Twenty-fourth Day of October, 2000

Attest:

Q. TODD DICKINSON

Attesting Officer

Director of Patents and Trademarks